(12) United States Patent
Goff et al.

(10) Patent No.: US 9,821,363 B2
(45) Date of Patent: Nov. 21, 2017

(54) RADIAL COMPRESSION DEVICE WITH CONSTRAINED DIES

(71) Applicants: Ed Goff, Phoenix, AZ (US); Jeremiah J. Warriner, Laveen, AZ (US)

(72) Inventors: Ed Goff, Phoenix, AZ (US); Jeremiah J. Warriner, Laveen, AZ (US)

( * ) Notice: Subject to any disclaimer, the term of this patent is extended or adjusted under 35 U.S.C. 154(b) by 0 days.

(21) Appl. No.: 15/276,539

(22) Filed: Sep. 26, 2016

(65) Prior Publication Data
US 2017/0087620 A1    Mar. 30, 2017

Related U.S. Application Data

(60) Provisional application No. 62/235,075, filed on Sep. 30, 2015.

(51) Int. Cl.
| | |
|---|---|
| B21D 41/04 | (2006.01) |
| B21J 7/16 | (2006.01) |
| A61F 2/95 | (2013.01) |
| B30B 7/00 | (2006.01) |
| B30B 7/04 | (2006.01) |
| B25B 27/10 | (2006.01) |

(52) U.S. Cl.
CPC ............. *B21D 41/04* (2013.01); *A61F 2/95* (2013.01); *B21J 7/16* (2013.01); *B25B 27/10* (2013.01); *B30B 7/00* (2013.01); *B30B 7/04* (2013.01); *A61F 2002/9522* (2013.01)

(58) Field of Classification Search
CPC  B21D 41/04; A61F 2/95; B25B 27/10; B30B 7/00; B30B 7/04; B30B 7/12; B21J 7/16
USPC .......................................................... 72/402
See application file for complete search history.

(56) References Cited

U.S. PATENT DOCUMENTS

| | | | | |
|---|---|---|---|---|
| 1,480,077 | A * | 1/1924 | Johnson | B21J 7/145 72/402 |
| 4,041,766 | A * | 8/1977 | Johnson | B21F 45/00 29/753 |
| 4,454,657 | A * | 6/1984 | Yasumi | B21C 3/06 29/751 |
| 5,715,723 | A * | 2/1998 | Owens | B21D 39/048 29/237 |
| 6,925,847 | B2 * | 8/2005 | Motsenbocker | A61F 2/95 29/283.5 |
| 7,963,142 | B2 * | 6/2011 | Goff | A61F 2/95 29/282 |
| 8,220,307 | B2 * | 7/2012 | Goff | B21D 41/04 29/282 |

(Continued)

*Primary Examiner* — David B Jones
(74) *Attorney, Agent, or Firm* — Parsons & Goltry; Robert A. Parsons; Michael W. Goltry (57) ABSTRACT

A radial compression mechanism includes a constraining structure with a cut-out defined by a plurality of bearing surfaces. A plurality of die are carried by the constraining structure and arranged in a circular pattern about a central axis. Each die has a base side positioned in parallel juxtaposition to a corresponding bearing surface and each die is constrained to move reciprocally and linearly along the corresponding bearing surface. Working surfaces of the plurality of die cooperate to form a cavity that is movable between an open position and a closed position. A driving mechanism is coupled to at least one of the plurality of die to drive all of the die in unison between the open position and the closed position.

16 Claims, 10 Drawing Sheets

(56) References Cited

U.S. PATENT DOCUMENTS 8,336,177 B2 * 12/2012 Vernasca .............. B21D 39/048
                                                      29/235
8,474,299 B2 *  7/2013 Lutze ................. H01R 43/0424
                                                      72/402

* cited by examiner

RADIAL COMPRESSION DEVICE WITH CONSTRAINED DIES

CROSS REFERENCE TO RELATED APPLICATION

This application claims the benefit of U.S. Provisional Patent Application No. 62/235,075, filed 30 Sep. 2015.

FIELD OF THE INVENTION

This invention generally relates to radial compression mechanisms and more specifically to mechanisms for compressing devices such as stents, catheters, balloons, and the like.

BACKGROUND OF THE INVENTION

In the manufacture and testing of medical devices, mechanisms are used to radially compress cylindrical devices such as stents, balloons, and catheters. For example, installation of a stent onto a catheter balloon is typically accomplished by compressing the stent radially inward onto the balloon with enough pressure to permanently deform the stent to a smaller diameter and to slightly embed the metal stent into the plastic balloon. In another example, a polymer catheter balloon is compressed radially after pleating to wrap it tightly around the catheter shaft. In another example, a self-expanding stent is radially compressed to insert it into a sheath or delivery system. In an example of medical device testing, a stent is radially compressed while the required force is measured, in order to measure the stent's functional relationship between diameter and radial force.

A first type of prior art device includes a radial compression mechanism wherein several similar wedge-shaped die with planar surfaces are arranged to form an approximately cylindrical central cavity, the wedges being hinged and driven in unison to change the diameter of the cavity. Examples of this mechanism are the Crimpfox tool sold by Phoenix Contact GmbH 7 Co. KG (CRIMPFOX UD 6-6, Part Number 1206366), and the "segmental compression mechanism" marketed by Machine Solutions Incorporated, and described in U.S. Pat. No. 6,968,607. In this type of mechanism, the working surfaces of the die have a wedge shape with two planar surfaces meeting at the tip. A shortcoming of this type of mechanism is that there exists a gap between adjacent wedges, the size of which varies with the diameter of the cavity in an undesirable way. Typically, the mechanism is specifically designed to provide a desired range of cavity diameters. At the lowest and highest diameters, the die are tightly wedged against each other (zero gap). As the diameter is increased from the lowest, the gap increases until it reaches a maximum, then decreases until it becomes zero again at the highest diameter. The diameter range and gap (as a function of diameter) depend on the specific design of the mechanism, particularly the location of the hinge point of the die and the diameter of the circle formed by all of the die hinge points in the mechanism. A larger diameter of the hinge point circle results in a smaller maximum gap for a given diameter range. The strict design tradeoffs for this type of mechanism results in a mechanism that must be large to provide a small maximum gap for a given diameter range, or a mechanism that must have a large gap to provide the same diameter range in a small size. Large gaps between the wedges are a disadvantage because they allow space for parts of the compressed device to go into. For example, the metal struts of a stent can move into the gap and be damaged.

A second type of prior art device includes a radial compression mechanism wherein several similar wedge-shaped die with planar surfaces are arranged to form an approximately cylindrical central cavity, the wedges being attached to linear guides that constrain each die individually to move linearly relative to a stationary part, the die being driven in unison to change the diameter of the central cavity. Each die's motion path is constrained when assembled to the stationary part, even when the other die are not present. The die are guided only by the linear guides, and not by neighboring die. Examples of this mechanism include the mechanism taught by Kokish in U.S. Pat. No. 6,651,478, or the mechanism marketed by Interface Catheter Solutions as part of the model DFW-1000 balloon fluter-wrapper machine. In this type of mechanism, the working surfaces of the die have a wedge shape with two planar surfaces meeting at the tip. The linear motion of the wedges in this mechanism provides a wedge-to-wedge gap that is constant, independent of the cavity diameter, and may be designed to be any desired size. A shortcoming of this mechanism is that it typically does not provide a sufficiently accurate positional relationship of the wedge-shaped working ends of the die. Accurate positional relationship of the die is important so that the central cavity remains approximately round and provides even compression around the circumference of the compressed device, and so that the largest die-to-die gaps aren't much larger than the average. Each die is carried on its own linear guide, all of the guides are attached to a plate or base, and another rotating part such as a cam must be used to impose motion in unison. Therefore, many parts and attachments may influence the accuracy (roundness) of the central cavity. Medical device manufacturing and testing often require an accurately round cavity at diameters as small as 0.3 mm, which this type of mechanism is typically unable to achieve because of dimensional variability of the many parts.

A third type of prior art device is a radial compression mechanism wherein several arcuate-shaped die have an outer end pivotally attached to a hinge plate and approximately wedge-shaped inner working tips that form an approximately cylindrical-shaped central cavity. The die are driven in unison to form and change the diameter of the central cavity. A mechanism of this type is described in U.S. Pat. No. 7,963,142 B2, and is marketed by Blockwise Engineering LLC as the "J-Crimp" mechanism. This type of mechanism has an important advantage over the first type of prior art: constant die-to-die gaps that do not vary with opening diameter. It also has an important advantage over the second type of prior art: it can be manufactured with die-to-die gaps smaller and more precise. Although the die-to-die gaps of this third type of mechanism can be made not to vary as function of the opening diameter, and are generally smaller than those of the other prior art, the tolerance of the die-to-die gaps remains significant because there are several parts contributing to manufacturing dimensional variability, including the die themselves, which are rather long and thin. Further improvement of the smallness and precision of the die-to-die gaps would be advantageous in some applications, such as stent crimping of very small stents or balloon wrapping of very small balloons, where the compressed product benefits from being very small, uniform, and accurately round.

It would be highly advantageous, therefore, to remedy the foregoing and other deficiencies inherent in the prior art.

Accordingly, it is an object of the present invention to provide a new and improved radial compression mechanism.

Another object of the invention is to provide a new and improved radial compression mechanism for compressing devices such as stents, catheters, balloons, and the like in the medical industry.

SUMMARY OF THE INVENTION

Briefly, to achieve the desired objects and advantages of the instant invention provided is a radial compression mechanism including a constraining structure having a cut-out formed therethrough. The cut-out is defined by a plurality of bearing surfaces. A plurality of die are carried by the constraining structure and arranged in a circular pattern about a central axis. Each die of the plurality of die has a base side positioned in parallel juxtaposition to a corresponding bearing surface of the plurality of bearing surfaces with each die constrained to move reciprocally and linearly along the corresponding bearing surface. Each die of the plurality of die have a working surface, the working surfaces of the plurality of die cooperating to form a central product-receiving cylindrically-shaped cavity that is movable between an open position and a closed position as the plurality of die move in unison. A driving mechanism is coupled to at least one of the plurality of die to drive the die in unison between the open position and the closed position.

More specifically, each of the plurality of die have a sliding surface opposite the working surface. The sliding surface of each die of the plurality of die is positioned in substantially parallel juxtaposition to the working surface of an adjacent die, a constant width gap is defined between the sliding surface of each die of the plurality of die and the working surface of each adjacent die of the plurality of die.

Yet more specifically, a radial compression mechanism is provided wherein the constraining structure includes a first stationary plate including a first cut-out formed therethrough, the first cut-out defined by a plurality of bearing surfaces, and a second stationary plate including a second cut-out formed therethrough, the second cut-out defined by a plurality of bearing surfaces. The first stationary plate and the second stationary plate are positioned in parallel, with the first cut-out and the second cut-out maintained in a parallel and aligned relationship. The plurality of die are carried within and extend between the first stationary plate and the second stationary plate.

BRIEF DESCRIPTION OF THE DRAWINGS

The foregoing and further and more specific objects and advantages of the instant invention will become readily apparent to those skilled in the art from the following detailed description of a preferred embodiment thereof taken in conjunction with the drawings, in which.

DETAILED DESCRIPTION OF A PREFERRED EMBODIMENT

Figure 1:
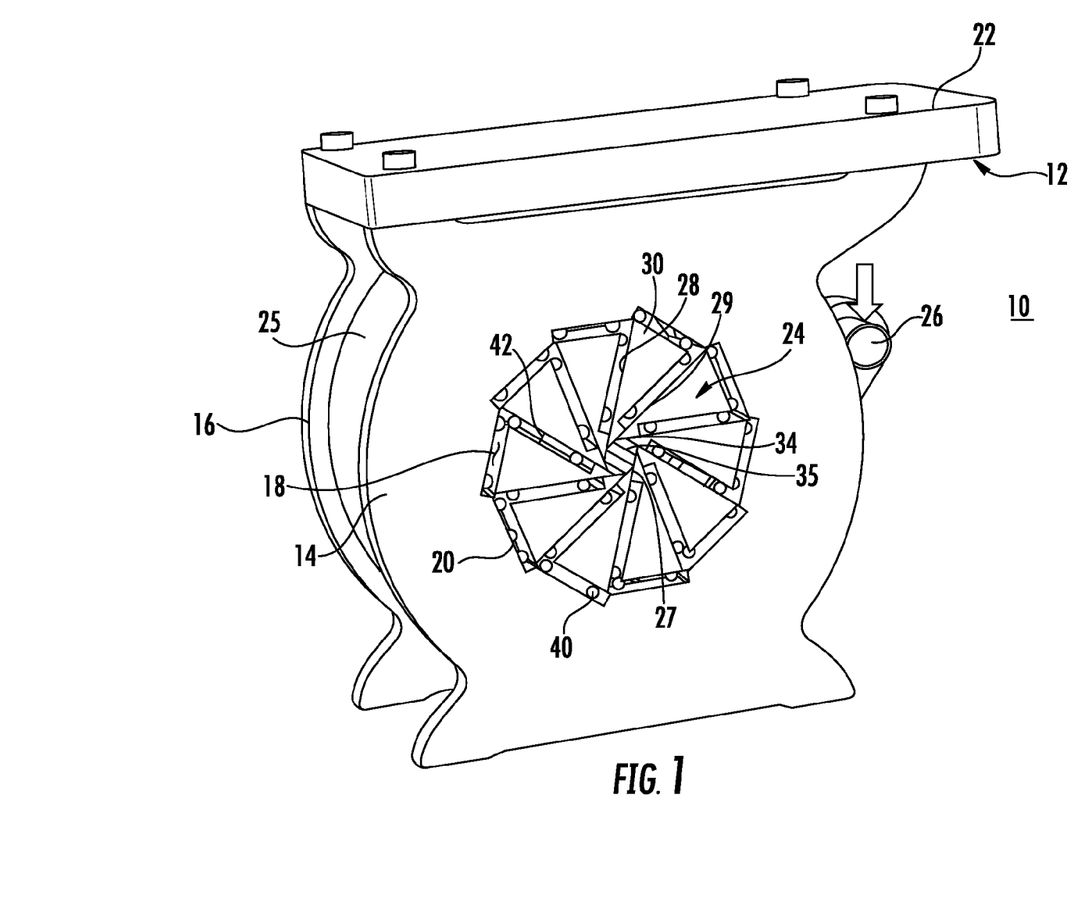
FIG. 1 is a side view in perspective of a radial compression device in accordance with the present invention, shown in an open orientation.
Figure 2:
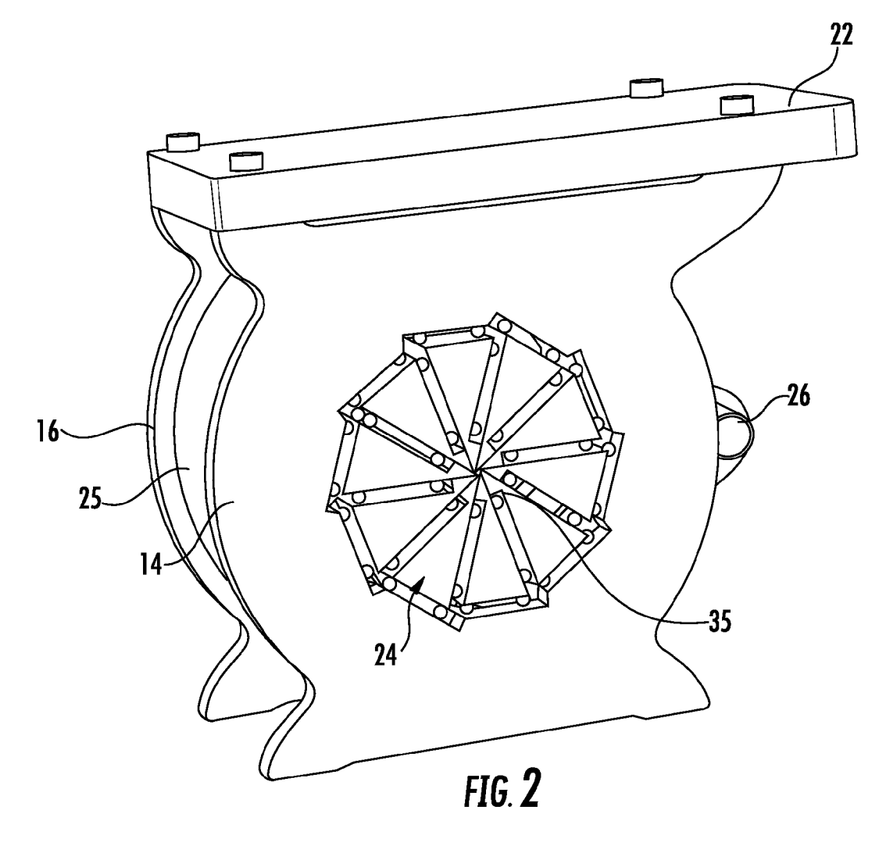
FIG. 2 is a side view in perspective of a radial compression device in accordance with the present invention, shown in a closed orientation.
Figure 6:
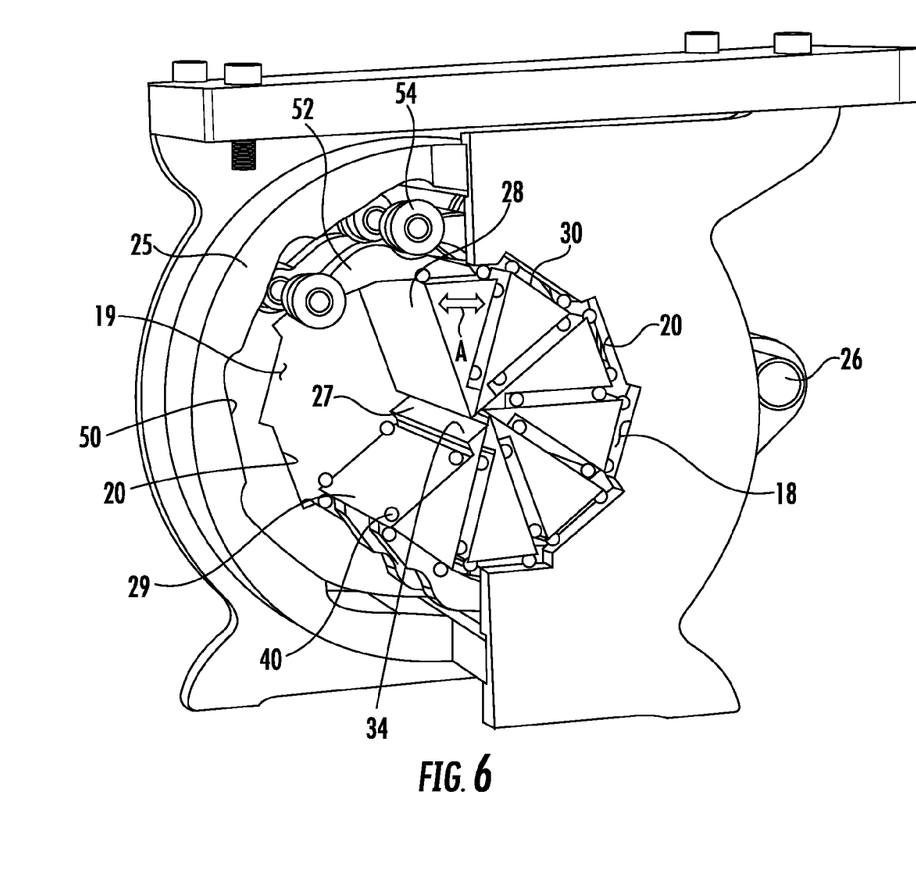
FIG. 6 is a side cutaway view in perspective of a radial compression device in accordance with the present invention, shown in a partly-open orientation, showing the die assemblies, the rolling balls, the stationary plates, and the rotating cam ring that actuates the die between the open and closed orientations.

Turning now to the drawings in which like reference characters indicate corresponding elements throughout the several views, attention is first directed to FIGS. 1, 2 and 6, which illustrate a radial compression device 10 in accordance with the present invention. Device 10 includes a constraining structure 12, which in this preferred embodiment includes a pair of spaced apart stationary plates 14 and 16. Each plate 14 and 16 includes a generally centrally located cut-out 18 and 19, respectively, formed therethrough and defined by a plurality of bearing surfaces 20. Each cut-out 18 and 19, defined by bearing surfaces 20, is a general polygonal shape, with each bearing surface 20 forming a side of the polygonal shape. Cut-outs 18 and 19 are parallel and aligned, with matching bearing surfaces 20. Plates 14 and 16 are mounted to a base 22 to prevent relative movement and provide a secure device. While two plates 14 and 16 are described, it will be understood that one or more plates can be employed in constraining structure 12, as long a cut-out defined by bearing surfaces is present.

Device 10 further includes a plurality of die 24 carried within cut-outs 18 and 19. Each die 24 extends between stationary plates 14 and 16, from cut-out 18 of plate 14 to cut-out 19 of plate 16. Plurality of die 24 are arranged in a generally circular pattern about a central axis, constrained by constraining structure 12 and movable between an open position and a closed position. A driving mechanism is coupled to at least one of the plurality of die 24 to drive all of the die in unison between the open position and the closed position. In the preferred embodiment, the driving mechanism includes a rotating cam element 25 reciprocally rotatably carried between stationary plates 14 and 16 and actuated by an arm 26 driven by an actuating force. The actuating force can be provided by substantially any means, including electric motor, mechanical, manual and the like. Die 24 are moved within cut-outs 18 and 19 by cam element 25 between the open position (FIG. 1) and the closed position (FIG. 2) which can have an accurately round cavity at diameters as small as 0.3 mm.

Figures 7, 8:
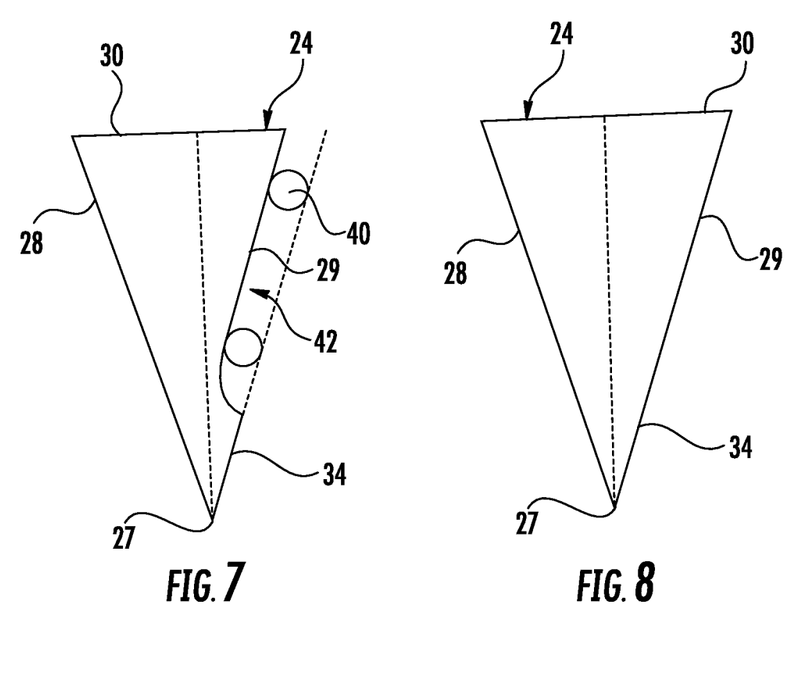
FIG. 7 illustrates an isosceles-triangular-shaped die, with a cutout to accommodate balls for guidance.
FIG. 8 illustrates an isosceles-triangular-shaped die, without a cutout to accommodate balls for guidance.

Still referring to FIGS. 1, 2 and 6, each die 24 is preferably an isosceles-triangle or wedge shape, with a vertex 27 defined by converging sides 28 and 29 (FIG. 8). Vertex 27 preferably has an angle of approximately 36 degrees in the preferred embodiment. Each die 24 also includes a base side 30 opposite vertex 27. The number of bearing surfaces 20 of cut-outs 18 and 19 is dependent upon the number of die 24 used. In the preferred embodiment, the polygonal shape of cut-outs 18 and 19 is a decagon carrying ten die 24. It will be understood that more or less die 24 can be used, with the polygonal shape corresponding to the number selected. It should be noted that the number of die may be varied over the practical range of 3 to 15 depending on the requirements and desires of the manufacturer. It should also be noted that the decagon described here would, in the general case, be a regular polygon with a number of sides equal to the die count, and that the vertex angle of the isosceles-triangular-shaped die would in general be equal to 360 degrees divided by the number of die.

Plurality of die 24 are arranged in a generally circular pattern about a central axis with sides 28 of die 24 in parallel juxtaposition with sides 29 of adjacent die 24. This arrangement of die 24 is constrained within cut-outs 18 and 19, such that base side 30 of each die of the plurality of die 24 is positioned adjacent one of the bearing surfaces 20 forming the sides of the polygonal cut-outs 18 and 19. The dimensions of cut-outs 18 and 19, and the dimensions of die 24, are chosen so that there is just enough space to pack die 24 within cut-outs 18 and 19 of stationary plates 14 and 16 and engaging bearing surfaces 20. With the proper dimensions, bases 30 of die 24 bear on and are guided by bearing surfaces 20 and sides 28 of die 24 bear on and are guided by sides 29 of adjacent die 24. One portion of side 29 of each die 24, near vertex 27, forms a working surface 34 that contacts a product, and cooperates with the other die' working surface 34 to define a central cylindrically-shaped product-receiving cavity 35 generally at the central axis of the circular pattern of arranged die 24.

Figure 3:
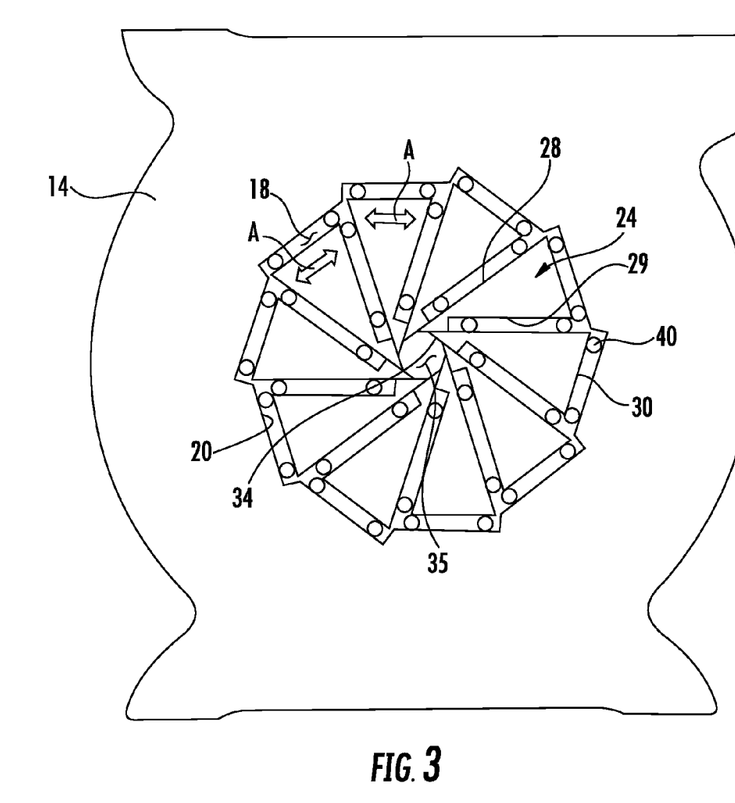
FIG. 3 is a side view of the essential parts of the preferred embodiment of the present invention, showing the roughly isosceles-triangular-shaped die, the stationary plate, and rolling balls both between the die and between the die outer edges and the stationary plate, shown in an open orientation.
Figure 4:
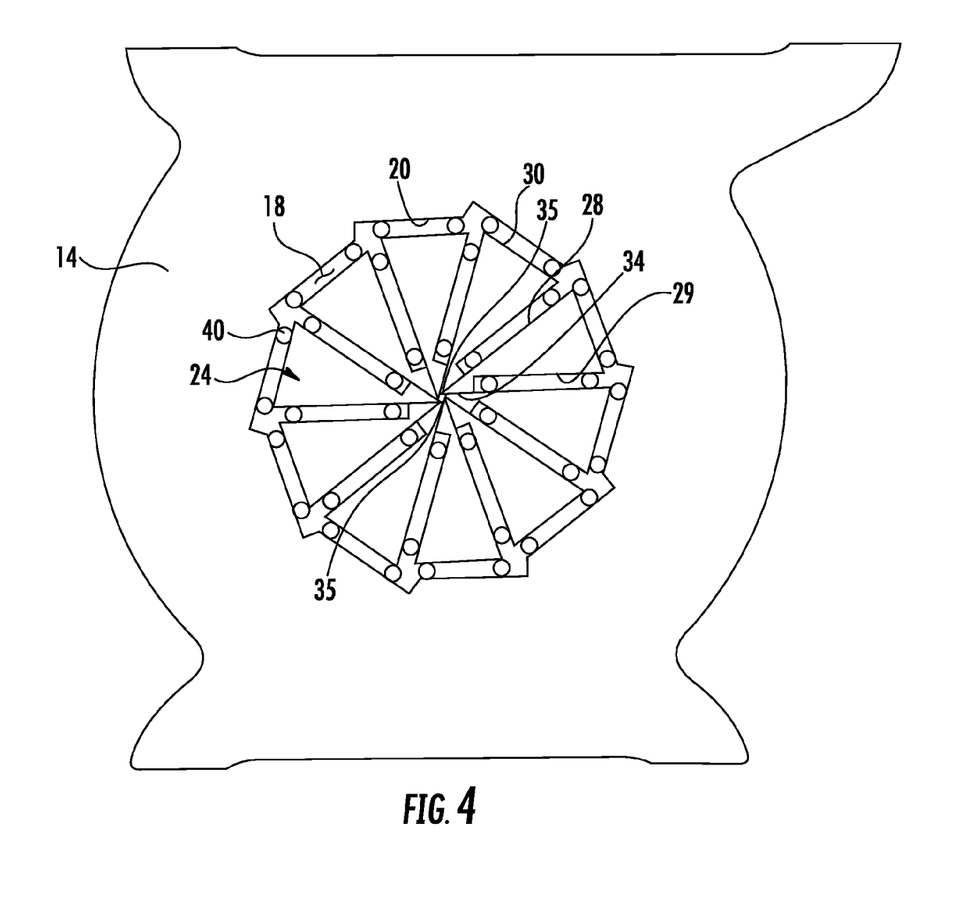
FIG. 4 is a side view of the essential parts of the preferred embodiment of the present invention, showing the roughly isosceles-triangular-shaped die, the stationary plate, and rolling balls both between the die and between the die outer edges and the stationary plate, shown in a closed orientation.

As illustrated in FIGS. 3 and 4, the above-described arrangement of stationary plates 14 and 16, and die 24 results in a certain constrained motion of die 24. Each die 24 is free to move only in linear motion relative to the stationary plates, and only along a direction parallel to bearing surfaces 20 as indicated by arrowed line A, and only in unison with each other. Furthermore, this arrangement constrains each die 24 to move only in linear motion with respect to each of the two adjacent die 24, namely a sliding motion between sides 28 and sides 29 of adjacent die. Further still, this constrained and coordinated die motion results in a changing diameter of the central cylindrically-shaped product-receiving cavity 35 between the open position and the closed position. The motion is so completely constrained that, if bearing surfaces 20 were free of friction, a force applied to any one of die 24 would cause the whole group of die to move in unison to open or close central cavity 35.

Figure 9:
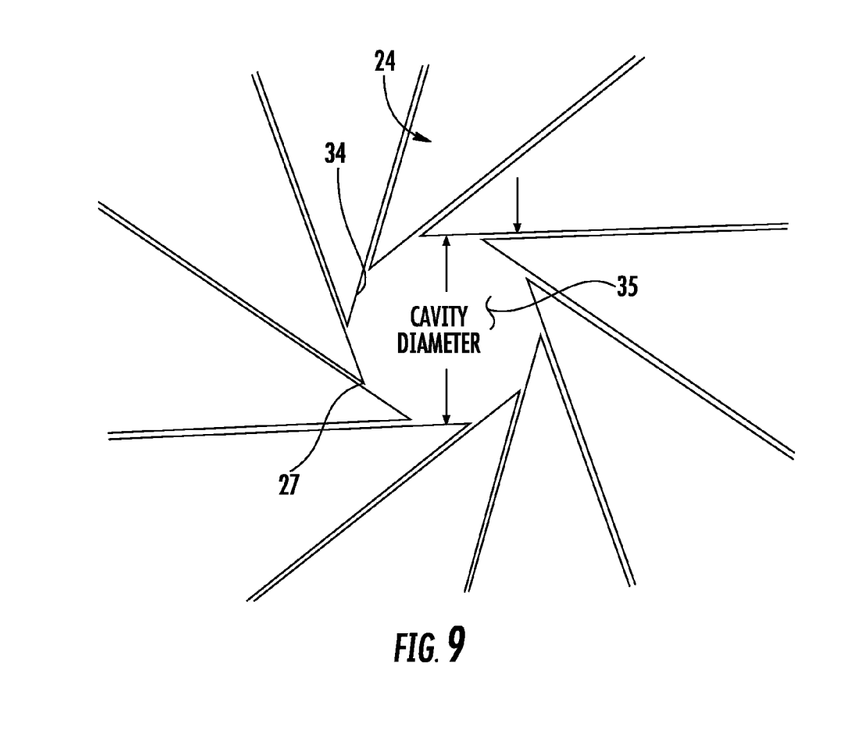
FIG. 9 is an enlarged side view of the working tips forming a cavity to illustrate the gap formed therebetween.
Figure 10:
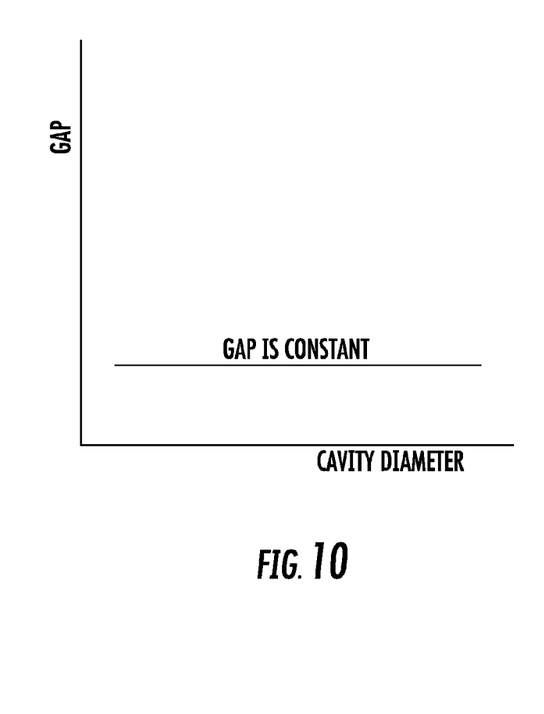
FIG. 10 is a graphical representation of the relationship between die-to-die gap and cavity diameter for the present invention.

The above-described arrangement of die 24 also results in a constant die-to-die gap that does not vary depending on the diameter of central cavity 35, as illustrated in FIGS. 9 and 10. The dimension of the die-to-die gap may be designed to be any size, depending on the requirements of the application, but for many applications it should be as small as possible while preventing direct rubbing contact of working tips 34, in accordance with the achievable manufacturing tolerances of the parts. In some applications, direct rubbing contact of the adjacent working tips 34 may be allowable or desirable.

Contact between die 24 can be made by direct sliding contact of planar surfaces, with or without lubricating grease or oil or can be made to slide easier on one another and bearing surfaces 20 by application of low friction materials, or by use of bearing elements such as rolling cylinders (also known commonly as "needle rollers") or by the use of balls 40 as in the preferred embodiment illustrated. Bearing balls 40 are used for die-to-die bearing and guidance. Balls 40 are positioned between adjacent sides 28 and 29 of adjacent die 24 as well as between base 30 and bearing surfaces 20. Die 24 and rolling bearing balls 40 are preferably made from hard material such as hardened tool steel or hardened martensitic stainless steel or ceramic. Bearing balls 40 provide low friction, long service life with low wear, low maintenance, and very good guiding precision. In this embodiment, the precision of the die-to-die gaps is influenced only by a small number of parts comprising die 24 themselves and rolling bearing balls 40.

Figure 11:
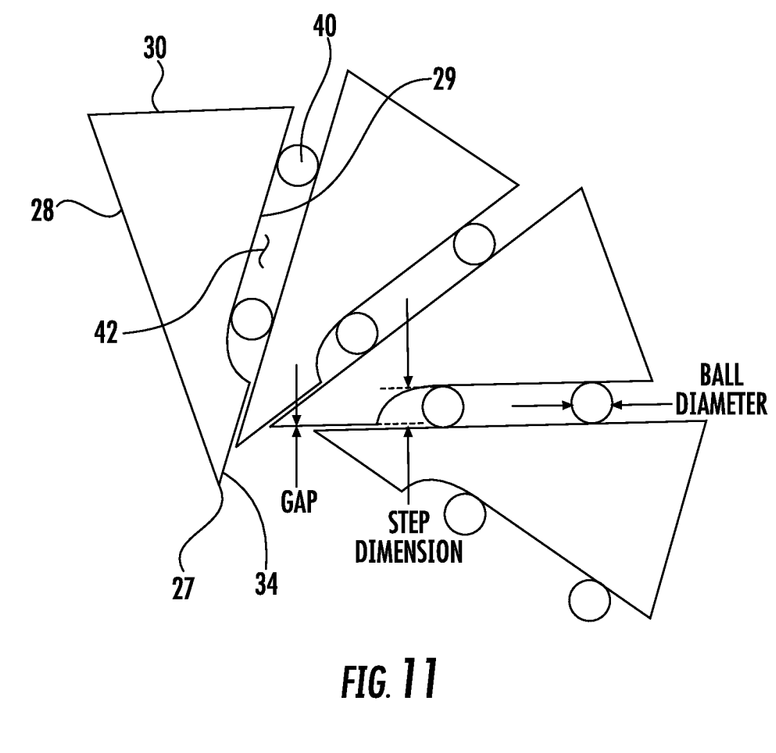
FIG. 11 illustrates, the primary influencers of the die-to-die gap, namely, the die's step dimension and the ball diameter.

With reference to FIGS. 7 and 11, die 24 can be modified to further reduce the gap created between die 24 by forming an inset step 42 along side 29 of each die 24. Bearing balls 40 are carried between die 24 within inset steps 42, each of which act as a ball race. In this manner, friction between die 24 is reduced by bearing balls 40 while a very slight, if any, gap is created at working tips 34. Only one aspect of die 24 is the primary factor influencing the gaps: the dimension of inset step 42 between working tip surface 34 and the ball-race surface, a feature that can easily be made to very high precision. For example, readily available metal cutting methods such as surface grinding or wire-cut EDM can make such cuts with accuracy plus or minus 0.0002 inches. Using those metal cutting methods, all of the relevant features of die 24 can be made without removing the part from the machine, thus avoiding dimension errors due to part fixturing on the cutting machine. Furthermore, bearing balls 40 of extremely high precision, for example, with diameter dimension 0.125 inch plus or minus 0.00005 inch, are commonly available and inexpensive. Because the die's step dimension and the ball diameter are the primary influence on the die-to-die gap dimension, the gap can be designed to be much smaller than that of prior-art mechanisms without danger of die-to-die rubbing that may cause excess friction and wear.

It should also be noted that the bearing and guidance that occurs between die 24 and stationary plates 14 and 16, and also between the sides of adjacent die 24, may practically be achieved with a wide range of design elements, such as 1) direct sliding surface contact of the parts with or without lubricating grease or oil, or 2) by coating, laminating, or attaching various commonly-used friction-reducing or wear-enhancing materials, or 3) rolling cylinders (also known commonly as "needle rollers", or 4) cam-follower type ball bearing or plain bearings rolling on planer surfaces, or 5) rolling balls placed between the adjacent parts, as is shown in the embodiment in FIGS. 1-4 and 6. It should also be noted that the shape of the die, although shown to be isosceles triangular in this easy-to-illustrate embodiment, could in general take a wide variety of shapes, provided that the directions of linear motion allowed by the three bearing and guiding mechanisms engaging each die form an isosceles triangle.

Figure 5:
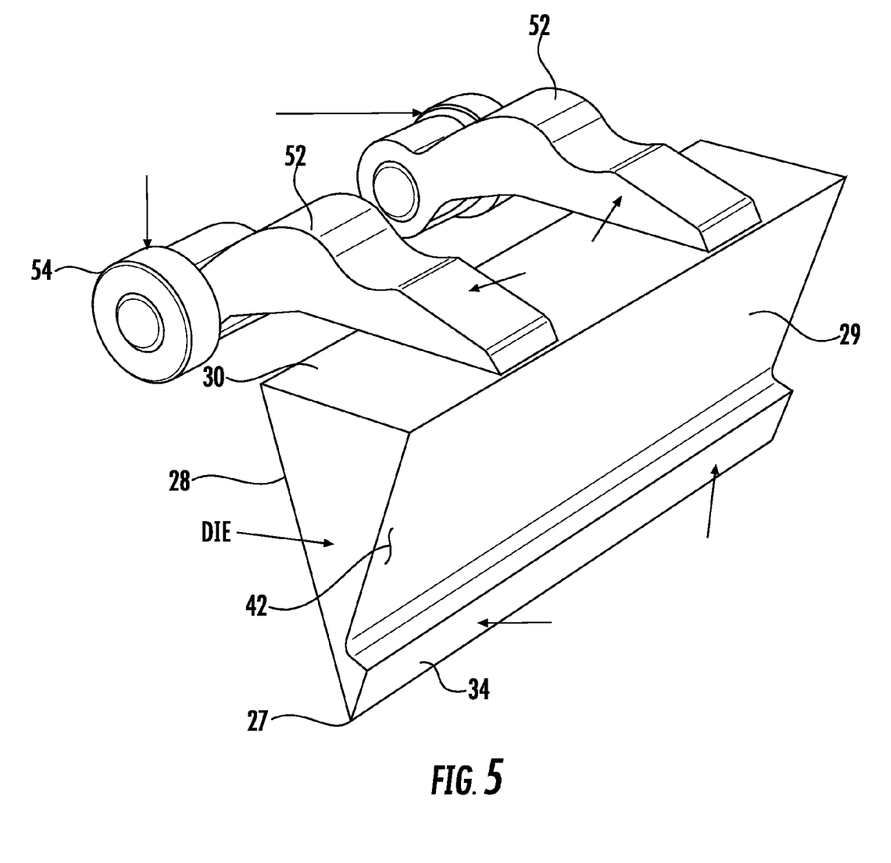
FIG. 5 is a perspective view of a complete die assembly of a preferred embodiment of the present invention showing the arms and rolling cam-follower bearings that move the die to create the open-to-closed motion.

Although central cavity 35 of device 10 can be opened or closed by a wide variety of actuating methods that apply a force to one or more die 24, one preferred embodiment uses rotating cam element 25 to simultaneously actuate all die 24. Simultaneous actuation of all die 24 imposes lower forces on the bearing and guiding apparatus compared to actuation of just one or a few of die 24, though this is possible. Referring to FIGS. 5 and 6, a rotating cam element 25 is rotatably coupled to and between stationary plates 14 and 16. Rotating cam 25 includes a cam surface 50 for each die 24. Referring specifically to FIG. 5, each die includes a pair of arms 52 terminating in rollers 54 also referred to as cam follower bearings. Arms 52 extend perpendicularly from base 30 and are intermediate stationary plates 14 and 16 when die 24 is mounted in housing 12. Cam surfaces 50 engage rollers or cam-follower bearings 54 of each die 24. Cam element 25 can be rotated to move die 24 between the open and the closed positions and continuously increase or decrease the diameter of central cavity 35. In this embodiment, an actuating arm 26 is attached to rotating cam element 25 such that a downward force on arm 26 from an actuator such as an air cylinder, handle, or electric motor closes central cavity 35. Arm 26 can be operated continuously to increase or decrease the diameter of the central cavity. In one example of use, with central cavity 35 at maximum, any device to be radially compressed, such as a stent, balloon, catheter, etc, is inserted into central cavity 35. Arm 26 is then operated to continuously reduce the diameter of central cavity 35 until the product is suitably compressed.

Figure 12:
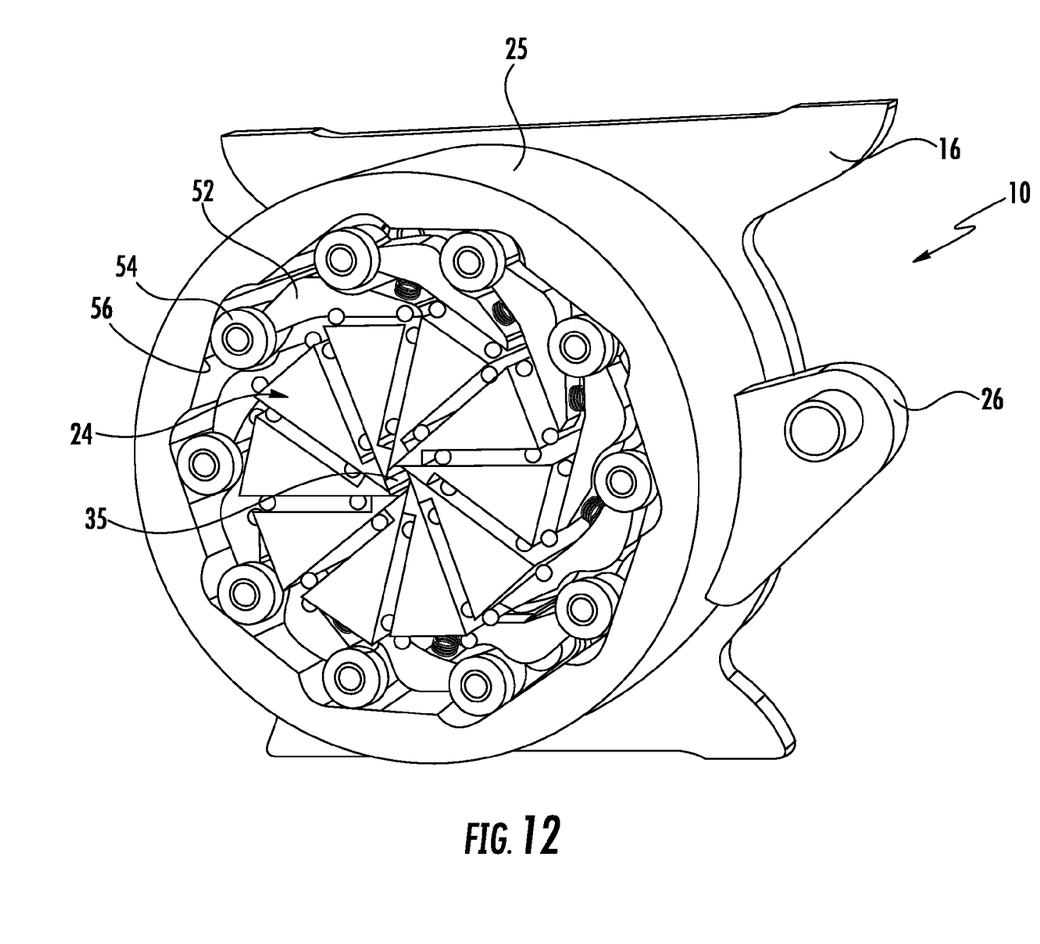
FIG. 12 is a side view of the radial compression device with the stationary plate removed illustrating return springs.

Turning to FIG. 12, die 24 are moved to a closed position by cam element 25, against a bias generated by return springs 60 carried between adjacent arms 52. Upon release of roller 54 from cam surfaces 50, springs 60 bias die 24 to the open position.

Thus, a new and novel radial compression mechanism has been disclosed. The new and novel radial compression mechanism is constructed to operate with a constant gap between adjacent die and to move the die in unison between a maximum diameter central cavity and a minimum diameter central cavity with a continuous radial movement, and to be manufacturable with very small and precise gaps between adjacent die. Therefore, the large and variable gaps of some prior art devices, and the relatively imprecise gaps of other prior art devices have been overcome.

Various changes and modifications to the embodiment herein chosen for purposes of illustration will readily occur to those skilled in the art. To the extent that such modifications and variations do not depart from the spirit of the invention, they are intended to be included within the scope thereof.

Having fully described the invention in such clear and concise terms as to enable those skilled in the art to understand and practice the same, the invention claimed is:

1. A radial compression mechanism comprising:
   a constraining structure including a cut-out formed therethrough, the cut-out defined by a plurality of bearing surfaces;
   a plurality of die carried by the constraining structure and arranged in a circular pattern about a central axis, each die of the plurality of die having a base side positioned in parallel juxtaposition to a corresponding bearing surface of the plurality of bearing surfaces, each die constrained to move reciprocally and linearly along the corresponding bearing surface;
   each die of the plurality of die having a working surface, the working surfaces of the plurality of die cooperating to form a central product-receiving cylindrically-shaped cavity that is movable between an open position and a closed position as the plurality of die move in unison; and
   a driving mechanism coupled to at least one of the plurality of die to drive all of the die in unison between the open position and the closed position.

2. A radial compression mechanism as claimed in claim 1, wherein each of the plurality of die have a sliding surface opposite the working surface, the sliding surface of each die of the plurality of die being positioned in substantially parallel juxtaposition to the working surface of an adjacent die, a constant width gap being defined between the sliding surface of each die of the plurality of die and the working surface of each adjacent die of the plurality of die.

3. A radial compression mechanism as claimed in claim 1, wherein the driving mechanism includes a cam element movable relative the constraining structure, the cam element has at least one cam surface engaging at least one of the plurality of die, wherein movement of the cam element simultaneously drives all of the die in unison between the open position and the closed position.

4. A radial compression mechanism as claimed in claim 1, wherein the driving mechanism includes a cam element movable relative the constraining structure, the cam element includes a plurality of cam surfaces, each cam surface corresponding to and engaging one die of the plurality of die, wherein movement of the cam element simultaneously drives all of the die in unison between the open position and the closed position.

5. A radial compression mechanism as claimed in claim 1, wherein the engagement between adjacent die of the plurality of die and between each die and the corresponding bearing surface is one of a direct sliding surface contact therebetween, coating, laminating, or attaching various friction-reducing or wear-enhancing materials therebetween, and positioning bearing elements therebetween.

6. A radial compression mechanism as claimed in claim 1, wherein the cut-out is a polygonal shapes and wherein each bearing surface forms a side of the polygonal shape.

7. A radial compression mechanism as claimed in claim 1, wherein the plurality of die includes between 3 and 15 die.

8. A radial compression mechanism as claimed in claim 1, wherein the central product-receiving cylindrically-shaped cavity is as small as 0.3 mm in the closed position.

9. A radial compression mechanism as claimed in claim 1, wherein the constraining structure comprises:
   a first stationary plate including a first cut-out formed therethrough, the first cut-out defined by a plurality of bearing surfaces; and
   a second stationary plate including a second cut-out formed therethrough, the second cut-out defined by a plurality of bearing surfaces.

10. A radial compression mechanism comprising:
    a first stationary plate including a first cut-out formed therethrough, the first cut-out defined by a plurality of bearing surfaces;
    a second stationary plate including a second cut-out formed therethrough, the second cut-out defined by a plurality of bearing surfaces;
    the first stationary plate and the second stationary plate positioned in parallel, with the first cut-out and the second cut-out maintained in a parallel and aligned relationship;
    a plurality of die carried within and extending between the first stationary plate and the second stationary plate, the plurality of die arranged in a circular pattern about a central axis, each die of the plurality of die having a base side positioned in parallel juxtaposition to a corresponding bearing surface of the plurality of bearing surfaces of the first stationary plate and the second stationary plate, each die constrained to move reciprocally and linearly along the corresponding bearing surfaces;

each die of the plurality of die having a working surface, the working surfaces of the plurality of die cooperating to form a central product-receiving cylindrically-shaped cavity that is movable between an open position and a closed position as the plurality of die move in unison; and a driving mechanism coupled to at least one of the plurality of die to drive all of the die in unison between the open position and the closed position.

11. A radial compression mechanism as claimed in claim 10, wherein each of the plurality of die have a sliding surface opposite the working surface, the sliding surface of each die of the plurality of die being positioned in substantially parallel juxtaposition to the working surface of an adjacent die, a constant width gap being defined between the sliding surface of each die of the plurality of die and the working surface of each adjacent die of the plurality of die.

12. A radial compression mechanism as claimed in claim 10, wherein the driving mechanism includes:

a rotating cam element carried between the first and second stationary plates for movement relative thereto; and a plurality of cam surfaces, each cam surface corresponding to and engaging one die of the plurality of die, wherein movement of the cam element simultaneously drives all of the die in unison between the open position and the closed position.

13. A radial compression mechanism as claimed in claim 10, wherein the engagement between adjacent die of the plurality of die and between each die and the corresponding bearing surfaces is one of a direct sliding surface contact therebetween, coating, laminating, or attaching various friction-reducing or wear-enhancing materials therebetween, and positioning bearing elements therebetween.

14. A radial compression mechanism as claimed in claim 10, wherein the cut-out is a polygonal shapes and wherein each bearing surface forms a side of the polygonal shape.

15. A radial compression mechanism as claimed in claim 10, wherein the plurality of die includes between 3 and 15 die.

16. A radial compression mechanism as claimed in claim 10, wherein the central product-receiving cylindrically-shaped cavity is as small as 0.3 mm in the closed position.

* * * * *